(12) United States Patent
Olson (10) Patent No.: US 11,937,910 B2
(45) Date of Patent: Mar. 26, 2024

(54) BIOLOGIC DELIVERY SYSTEM WITH POSITIONAL SENSING AND FORCE SENSING

(71) Applicant: ST. JUDE MEDICAL, CARDIOLOGY DIVISION, INC., St. Paul, MN (US)

(72) Inventor: Richard J. Olson, Blaine, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 1330 days.

(21) Appl. No.: 16/087,804

(22) PCT Filed: Apr. 5, 2017

(86) PCT No.: PCT/US2017/026155
§ 371 (c)(1),
(2) Date: Sep. 24, 2018

(87) PCT Pub. No.: WO2017/184342
PCT Pub. Date: Oct. 26, 2017

(65) Prior Publication Data
US 2020/0297239 A1 Sep. 24, 2020

Related U.S. Application Data

(60) Provisional application No. 62/325,026, filed on Apr. 20, 2016.

(51) Int. Cl.
*A61B 5/06* (2006.01)
*A61B 5/00* (2006.01)
(Continued)

(52) U.S. Cl.
CPC ............ *A61B 5/063* (2013.01); *A61B 5/4839* (2013.01); *A61B 5/6852* (2013.01);
(Continued)

(58) Field of Classification Search
CPC ....... A61B 5/063; A61B 90/06; A61B 5/4839; A61B 5/6582; A61B 5/6885; A61B 5/74
See application file for complete search history.

(56) References Cited

U.S. PATENT DOCUMENTS 6,171,276 B1  1/2001  Lippe et al.
2002/0013615 A1*  1/2002  Haim ................ A61M 25/0084
604/164.01
(Continued)

OTHER PUBLICATIONS

International Search Report for International Application No. PCT/US2017/026155, dated Sep. 5, 2017.

*Primary Examiner* — Alex M Valvis
*Assistant Examiner* — Justin Xu
(74) *Attorney, Agent, or Firm* — Billion & Armitage (57) ABSTRACT

Systems, apparatuses and methods are provided for identifying the position of a catheter relative to internal tissue and controlling injection of a therapeutic substance(s) into the internal tissue. In one embodiment, a catheter includes one or more position sensing electrodes disposed at or near a distal end of the catheter that allow identifying the position of the catheter relative to the internal tissue. The catheter also includes one or more contact sensors that provide an indication of contact and/or contact forces between the catheter and internal tissue before and after a therapy delivery needle is extended from the catheter into the internal tissue. Outputs of the contact sensor(s) allows for confirming insertion of the therapy delivery needle into the internal tissue to a desired depth. Once inserted to the desired depth, a therapeutic substance may be injected into the internal tissue at the desired depth.

11 Claims, 8 Drawing Sheets

(51) Int. Cl.
 *A61B 34/20* (2016.01)
 *A61B 90/00* (2016.01)
 *A61M 25/00* (2006.01)
 *A61M 25/01* (2006.01)

(52) U.S. Cl.
 CPC .............. *A61B 5/6885* (2013.01); *A61B 5/74* (2013.01); *A61B 90/06* (2016.02); *A61B 2090/065* (2016.02)

(56) References Cited

U.S. PATENT DOCUMENTS

| | | | |
|---|---|---|---|
| 2003/0014010 A1* | 1/2003 | Carpenter | A61M 25/0084 604/95.04 |
| 2005/0004513 A1* | 1/2005 | Beyerlein | A61B 5/4839 604/117 |
| 2006/0030833 A1 | 2/2006 | Harris et al. | |
| 2008/0108910 A1 | 5/2008 | Hein et al. | |
| 2013/0085413 A1 | 4/2013 | Tsamir et al. | |

* cited by examiner

BIOLOGIC DELIVERY SYSTEM WITH POSITIONAL SENSING AND FORCE SENSING

BACKGROUND a. Field

The present disclosure is directed to delivering therapeutic substances to internal tissue via a catheter device. More specifically, the present disclosure is directed to a catheter and delivery system and their method of use, which allow delivery of therapeutic substances to specifically targeted internal tissue locations and injection of the therapeutic substances to a desired depth.

b. Background Art

Gene therapy is a treatment that involves altering the genes inside cells of a body to stop or counteract disease. Generally, gene therapy replaces a faulty gene or adds a new gene in an attempt to cure disease or improve a body's ability to fight disease. Gene therapy holds promise for treating a wide range of diseases, including, without limitation, cancer, cystic fibrosis, heart disease and diabetes.

The specific procedure incorporating gene therapy depends on the disease being treated. By way of example, gene therapy may include having blood drawn or bone marrow removed. Then, in a laboratory, cells from the blood or bone marrow are exposed to a viral vector or another type of vector that contains the desired genetic material. Once the vector has entered the cells in the laboratory, those cells are injected back into the body via a vein or directly into tissue, where cells take up the vector along with the altered genes. Other vectors include, without limitation, stem cells and Liposomes. An exemplary use of gene therapy is the treatment of Ischemia.

Ischemia is a restriction in blood supply to tissues, causing a shortage of oxygen and glucose needed for cellular metabolism. Ischemia is generally caused by problems with blood vessels, with resultant damage to or dysfunction of tissue. Ischemic heart or cardiac ischemia occurs when the heart muscle, or myocardium, receives insufficient blood flow. Gene therapy for the treatment for ischemia and ischemic heart disease involves the delivery of gene therapy substances to tissue (e.g., myocardial heart tissue) to induce angiogenesis. Angiogenesis is a complex biological process that results in the growth of new blood vessels within tissue. Angiogenesis has been induced in heart tissue for reperfusion of tissue compromised by myocardial ischemia. Several growth factors or mediators are known to elicit angiogenic responses, and administration of these mediators promotes revascularization of ischemic tissues.

Delivery of gene therapy substances remains a significant challenge as these substances often have a short half-life. Accordingly, it is desirable to inject these substances directly into tissue to be treated to improve uptake of the therapeutic substance/solution. For example, previous application of gene therapy substances to ischemic heart tissue has typically included an open-chest procedure. According to this procedure, the patient's chest is opened surgically to expose the heart. The solution containing the vector is then delivered to the heart tissue by using a syringe to make a number of injections in a grid-like pattern, with the surgeon keeping track of the location of each injection. Once injected, the vector causes the cells in the target tissue to produce a desired growth factor to induce Angiogenesis.

Other delivery methodologies have included the use of catheters to deliver a therapy substance proximate to internal tissue to be treated. In such procedures, a catheter is guided (e.g., fluoroscopically) proximate to internal tissue to be treated and the tissue is bathed in the therapeutic solution expelled from the catheter. While reducing invasiveness, such a catheter procedure fails to directly inject target tissue with the therapeutic solution. This is due, in part, to the inability to specifically identify the location of a catheter within internal tissue and the inability to control the depth of injection of the therapeutic solution at a desired internal location. For instance, when treating cardiac tissue, the therapeutic substance is most commonly targeted to the myocardium, which is muscle tissue of the heart forming a thick middle layer between an outer epicardium layer and the inner endocardium layer. Accordingly, to effectively treat the myocardium, precise control of the injection depth is required. The injection cannot be too deep or too shallow.

SUMMARY

Various catheters and/or catheter-based systems, are disclosed herein that may include various combinations of features to control the positioning of a catheter relative to an internal tissue location (e.g., target tissue) and to control injection of a therapeutic substance(s) into the target tissue. In various embodiments, a catheter may include an elongate shaft and one or more position sensing electrodes positioned at or near a distal end of the shaft. The position sensing electrodes may include, for example, a tip electrode, one or more ring electrodes and/or button-type or spot electrodes. The catheter may also include one or more contact sensors, such as mechanical/pressure, impedance and/or optical sensors to provide an indication of contact and/or contact forces between the catheter and targeted tissue. Additionally, the catheter includes a therapy delivery needle that is selectively extendable relative to a distal end of the catheter. The needle may be extended a desired distance beyond a distal end or tip of the catheter to deliver therapeutic substances to tissue. In one arrangement, use of the contact sensor(s) allows for confirming insertion of the therapy needle into the target tissue to a desired depth. Once inserted to the desired depth, a therapeutic substance may be injected into the target tissue at the desired depth.

According to a first aspect, a system is provided for the delivery and injection of therapeutic substances into internal tissue of a body. The system includes a catheter having a flexible elongated shaft with a proximal end (e.g., handle) and a distal end adapted for insertion within a patient body. A lumen extends through at least a portion of the catheter shaft and exits the catheter shaft at an opening near the distal end. Disposed within the lumen is a therapy delivery needle, which is selectively movable between a retracted position (i.e., disposed within the catheter shaft) and an extended position where a portion of the needle is disposed a predetermined distance beyond the opening of the lumen. The predetermined distance/extension of the needle may correspond to a desired injection depth. The therapy delivery needle is fluidly connected to a supply of therapeutic solution, which may be controllably injected through the needle. The catheter further includes at least a first contact sensor that is disposed proximate to the distal end of the catheter. The contact sensor(s) generates contact outputs that are indicative of contact conditions between the catheter and an internal target tissue. A control unit monitors the contact outputs of the contact sensor. More particularly, the control unit identifies a first contact output where the catheter contacts a target tissue and the therapy delivery needle is in the retracted position within the lumen (i.e., prior to extension through the opening). The control unit compares subsequent contact outputs obtained after the therapy delivery needle is extended a predetermined distance through the opening of the lumen. Based on these comparisons, the control unit determines a degree of needle insertion into the target tissue and may generate an output indicative of the needle insertion. For instance, the control unit may generate an output indicating that therapy needle is fully inserted within the target tissue upon which the therapeutic solution may be injected through the needle into the target tissue. Alternatively, the control unit may generate an output indicating the needle is less than fully inserted within the target tissue which may allow a clinician to adjust the position of the catheter such that the needle is fully inserted within the target tissue.

The contact sensor(s) is configured to detect contact between the distal end of the catheter and target tissue. In one arrangement, the contact sensor is a force sensor that allow assessing the degree of mechanical coupling between catheter and the target tissue. Various force sensors may be utilizes and such sensors may generate signals indicative of a change in resistance, voltage, capacitance or a combination thereof. That is, the force sensors may comprise, for example, capacitance sensors that generate a signal indicative of a change in capacitance resulting from application of a force. Alternatively, the force sensors may comprise piezoelectric sensors that include a piezoelectric material (in the form of a wire, film or tubes, for example) and generate a signal indicative of a change in voltage resulting from placing the piezoelectric material under stress. In another embodiment, the force sensors may also comprise pressure transducers such as a pressure sensitive conductive composite (PSCC) sensors where the electrical resistance of the composite varies inversely in proportion to the pressure that is applied to the composite. In another arrangement, the force sensors may comprise optical sensors that detect deflection in the distal end of the catheter. In another arrangement, the contact sensor may comprise an electrode. In such an arrangement, an electrical property of the electrode may change based on its contact with tissue. For instance, the impedance of such an electrode may change based on the degree of contact with tissue. Along these lines, the control unit may be used to resolve an electrode output signal into component parts of impedance at the catheter/tissue interface allowing the control to determine values for one or more components of a complex impedance between the electrode (e.g., tip electrode) and tissue. Such impedance components or values may be correlated to know contact conditions.

In a further arrangement, the system includes a positioning system allows for identifying the location of the catheter relative to a model of an internal tissue location including the target tissue. In this arrangement, the catheter includes one or more position sensors attached to the catheter proximate to the distal end. These position sensors generate position output signals in response to applied signals. A navigation system receives the position outputs from the position sensors and locates a catheter within the coordinate system including the target tissue. Additionally, the navigation system includes a display that is configured to display a representation of the catheter relative to a model of the internal tissue location. Such a navigation and positioning system allows a clinician to visualize the catheter relative to an internal tissue location and/or adjust the position of the catheter relative to the internal tissue location to target one or more tissue targets for therapy injection. In one arrangement, the position sensors are coils that generate outputs in response to magnetic fields. In another arrangement, the position sensors are electrodes that generate outputs in response to electric fields.

In a further arrangement, sensors may be attached to the therapy delivery needle. In such an arrangement, a force sensor may be attached to the therapy delivery needle to identify forces applied to the distal tip of the needle. In a further arrangement, electrical wiring may be attached to the therapy delivery needle such that the therapy delivery needle forms an electrode such as an impedance sensor. In such an arrangement, impedance of the needle may change as the needle is extended beyond the catheter and/or inserted into target tissue. In a further arrangement, the catheter may include a sensor that identifies the extension of the needle beyond the lumen opening. Such sensors may include magnetic sensors that identify passage of magnetic strips attached to the therapy delivery needle.

In another aspect, a method is provided for delivering an injectable therapeutic substances into internal tissue of a body. The method includes receiving position outputs from position sensors attached proximal to a distal end of a catheter disposed within the body. The position outputs are utilized to generate a display of the catheter relative to a model of the internal tissue region where the catheter is disposed. Such a display may be utilized to position the catheter proximate to one or more target tissue locations. Once positioned at a target location, a first contact condition is identified between the catheter and the target tissue. Once correctly positioned and the first contact condition is identified, a therapy needle may be advanced a predetermined distance relative to the distal end of the catheter. After advancement of the therapy needle, a second contact condition between the catheter and target tissue is identified. Based on the first and second contact conditions, a degree of needle insertion may be identified. The degree of needle insertion may be output to a clinician allowing the clinician to determine if the needle is fully inserted into the target tissue or if the needle is less than fully inserted into the target tissue. If the needle is fully inserted, the clinician may inject a therapeutic substance through the needle. If the needle is not fully inserted, the clinician may reposition the catheter until the needle is fully inserted The foregoing and other aspects, features, details, utilities, and advantages of the present disclosure will be apparent from reading the following description and claims, and from reviewing the accompanying drawings.

DETAILED DESCRIPTION

Reference will now be made to the accompanying drawings, which at least assist in illustrating the various pertinent features of the presented disclosure. The following description is presented for purposes of illustration and description and is not intended to limit the disclosed systems, apparatuses and methods to the forms disclosed herein. Consequently, variations and modifications commensurate with the following teachings, and skill and knowledge of the relevant art, are within the scope of the presented disclosure. The embodiments described herein are further intended to explain the best modes known of practicing the disclosed systems, apparatuses and methods and to enable others skilled in the art to utilize the disclosed systems, apparatuses and methods in such, or other embodiments and with various modifications required by the particular application(s) or use(s).

The present disclosure is directed to a catheter-based therapeutic delivery system and method that utilizes positional sensing and contact sensing to ensure delivery of a therapeutic substance to a desired internal location (e.g., target tissue) and to a desired injection depth. Generally, the system uses one or more position sensors to spatially locate a catheter supported therapy delivery needle relative to targeted internal tissue. Once the therapy delivery needle is located at a desired internal location, the needle may be inserted into the target tissue. Use of contact sensing provides confirmation that the therapy delivery needle is inserted into the target tissue to a desired depth prior to injection of the therapeutic substance. The disclosed system and method have application in the controlled delivery of gene therapy as well as other substances (e.g., drugs).

Figure 1:
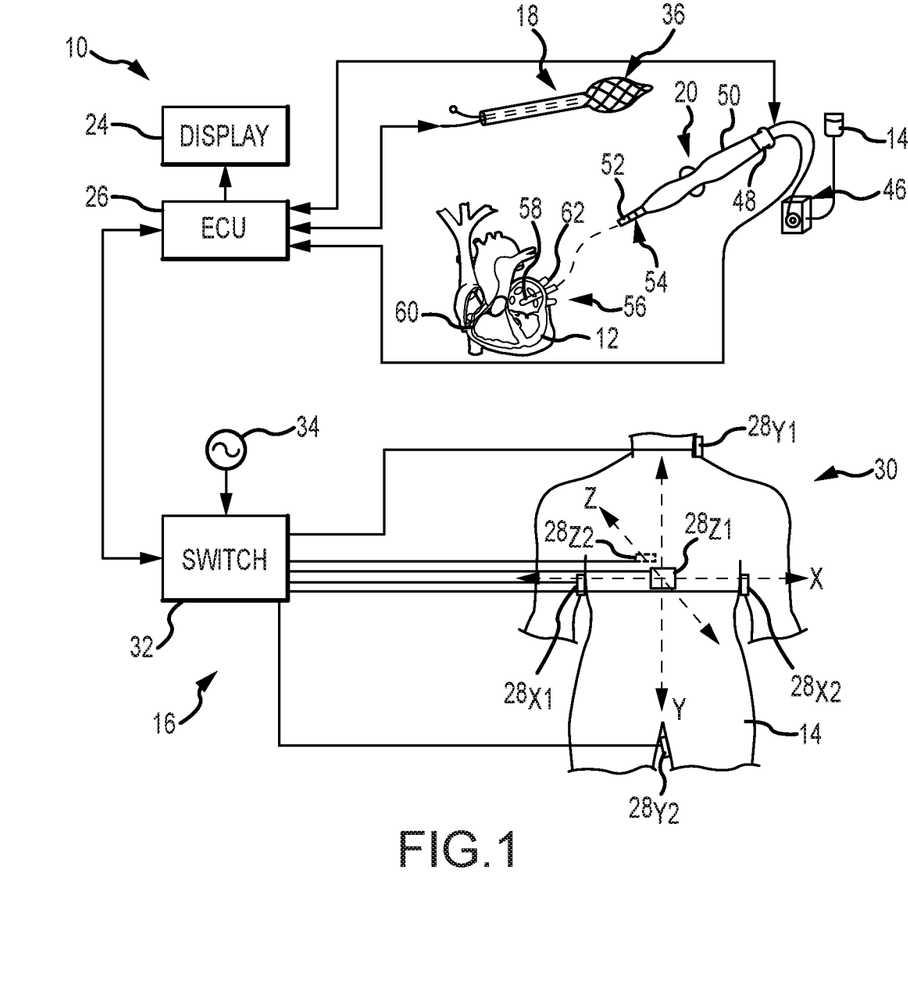
FIG. 1 is a diagrammatic illustration of an exemplary catheter system which may be implemented to access internal patient tissue for injection of therapeutic substances.

FIG. 1 illustrates a system 10 for diagnosis or treatment of tissue 12 in a body 14 in accordance with one embodiment of the present disclosure. In the illustrated embodiment the tissue 12 comprises cardiac tissue and the body 14 comprises a human body. It should be understood, however, that a system 10 in accordance with the present teachings may find application in connection with procedures for the diagnosis or treatment of a variety of tissues in human and non-human bodies. The system 10 may include a medical device position and navigation system 16, one or more medical devices including, for example, an electrophysiological (EP) mapping catheter 18 and a therapy injection catheter 20, a supply of a therapeutic substance 44 (e.g., gene therapy solutions, drugs, etc.), a display system 24, and an electronic control unit (ECU) 26.

The medical device position and navigation system 16 is provided to determine the position and orientation of medical devices within the body 14 such as catheters 18, 20 and may also be used to generate an electrophysiological map of a region of interest. The system 16 may display geometries or models of a region of interest in the body 14 on a display such as display system 24 along with representations of the catheters 18, 20 indicative of the position of the catheters 18, 20 relative to the region of interest. See, e.g., FIG. 2.

Referring again to FIG. 1, the system 16 may comprise a system that employs electric fields to detect the position of the catheters 18, 20 within the body 14 and may, for example, comprise the system available under the trademark "ENSITE NAVX" (a/k/a EnSite Classic as well as other versions of the EnSite™ system denoted as ENSITE VELOCITY' and ENSITE PRECISION') by St. Jude Medical, Inc. and generally shown in, for example, U.S. Pat. No. 7,263,397 titled "Method and Apparatus for Catheter Navigation and Location Mapping in the Heart," the entire disclosure of which is incorporated herein by reference. This embodiment of the system 16 is based on the principle that when low amplitude electrical signals are passed through the thorax, the body 14 acts as a voltage divider (or potentiometer or rheostat) such that the electrical potential or field strength measured at electrodes on the catheters 18, 20 may be used to determine the position of the electrode, and therefore the catheters 18, 20, relative to a pair of external patch electrodes using Ohm's law and the relative location of a reference electrode (e.g. in the coronary sinus).

In one configuration, the system 16 includes three pairs of patch electrodes 28 (namely $28_{X1}$, $28_{X2}$, $28_{Y1}$, $28_{Y2}$, $28_{Z1}$, $28_{Z2}$) that are placed on opposed surfaces of the body 14 (e.g., chest and back, left and right sides of the thorax, and neck and leg) and form generally orthogonal x, y, and z axes as well as a reference electrode/patch (not shown) that is typically placed near the stomach and provides a reference value and acts as the origin of a coordinate system 30 for the system 16. The electrodes 28 are used to create axes specific electric fields within the body 14. Electrodes $28_{X1}$, $28_{X2}$ may be placed along a first (x) axis. Similarly, electrodes $28_{Y1}$, $28_{Y2}$ may be placed along a second (y) axis, and electrodes $28_{Z1}$, $28_{Z2}$ may be placed along a third (z) axis. Each of the electrodes 28 may be coupled to a multiplex switch 32. The ECU 26 is configured through appropriate software to provide control signals to the switch 32 and thereby sequentially couple pairs of electrodes 28 to a signal generator 34. Sinusoidal currents are driven through each pair of patch electrodes 28 to generate an electromagnetic field within the body 14 and voltage measurements for one or more position sensors (e.g., electrodes) associated with the catheters 18, 20 are obtained. The measured voltages are a function of the distance of the position sensors from the patch electrodes 28. The measured voltages are compared to the potential at the reference electrode and a position of the position sensors within the coordinate system 30 of the navigation system 16 is determined.

In an alternative embodiment, the system 16 may comprise a system that employs magnetic fields to detect the position of the catheters 18, 20 within the body 14 such as the system available under the trademark "GMPS" or "MEDIGUIDE" by St. Jude Medical, Inc. and generally shown and described in, for example, U.S. Pat. No. 6,233,476 titled "Medical Positioning System," U.S. Pat. No. 7,197,354 titled "System for Determining the Position and Orientation of a Catheter," and U.S. Pat. No. 7,386,339 titled "Medical Imaging and Navigation System," the entire disclosures of which are incorporated herein by reference or the system available under the trademark "CARTO XP" by Biosense Webster, Inc. and generally shown and described in, for example, U.S. Pat. No. 5,391,199 titled "Apparatus and Method for Treating Cardiac Arrhythmias," U.S. Pat. No. 5,443,489 titled "Apparatus and Method for Ablation," U.S. Pat. No. 5,558,091 titled "Magnetic Determination of Position and Orientation," U.S. Pat. No. 6,498,944 titled "Intrabody Measurement," U.S. Pat. No. 6,788,967 titled "Medical Diagnosis, Treatment and Imaging Systems," and U.S. Pat. No. 6,690,963 titled "System for Determining the Location and Orientation of an Invasive Medical Instrument," the entire disclosures of which are incorporated herein by reference. In such a system, a magnetic field generator may be employed having three orthogonally arranged coils, arranged to create a magnetic field within body 14 and to control the strength, orientation, and frequency of the field. The magnetic field generator may be located above or below the patient (e.g., under a patient table) or in another appropriate location. Magnetic fields are generated by the coils and current or voltage measurements for one or more position sensors (e.g., coils) associated with the catheters 18, 20 are obtained. The measured currents or voltages are proportional to the distance of the sensors from the coils thereby allowing a position of the sensors within the coordinate system 30 of the system 16. In yet another alternative embodiment, system 16 may comprise a combination electric-field and magnetic-field based system.

In one arrangement, an EP mapping catheter 18 may be provided for use in gathering EP data associated with the tissue 12. The mapping catheter 18 includes a plurality of EP mapping electrodes 36. The electrodes 36 are placed in the body 14 (e.g., within the heart) within electrical fields created by exciting the patch electrodes 28. The electrodes 36 experience voltages that are dependent on the location between the patch electrodes 28 and the position of the electrodes 36 relative to the surface of the tissue 12. Voltage measurement comparisons made between the electrodes 36 can be used to determine the position of the electrodes 36 relative to the tissue 12. Movement of the electrodes 36 within the heart (e.g., within a heart chamber) or other internal tissue location produces information regarding the geometry of the internal region of interest. That is, the system 16 collects electrical data from the catheter(s) 18 and uses this information to track catheter movement and construct three-dimensional (3-D) models of the heart chamber or other internal tissue location in which the catheter is positioned. Additionally a physician may sweep the catheter(s) 18 across the heart chamber during data collection to outline the structures and relay the signals to the computer system, which generates the 3-D model. The resulting model may then be utilized to, for example, guide the therapy catheter 20 to one or more internal tissue locations where treatment is needed. Such a system allows for the creation of detailed internal models at the time of study and/or performance of an internal procedure. That is, the system is operative to generate substantially real-time models. The EP catheter 18 may be a non-contact mapping catheter such as the catheter available from St. Jude Medical, Atrial Fibrillation Division, Inc. under the registered trademark "ENSITE ARRAY." It should be understood, however, that the presented systems, apparatuses and methods may also be used with contact mapping systems in which measurements are taken through contact of electrodes with the tissue surface. In any arrangement, a map or model of the tissue 12 may be generated and this map/model may be utilized for subsequent delivery of a therapeutic substance to one or more target locations.

Figure 3A:
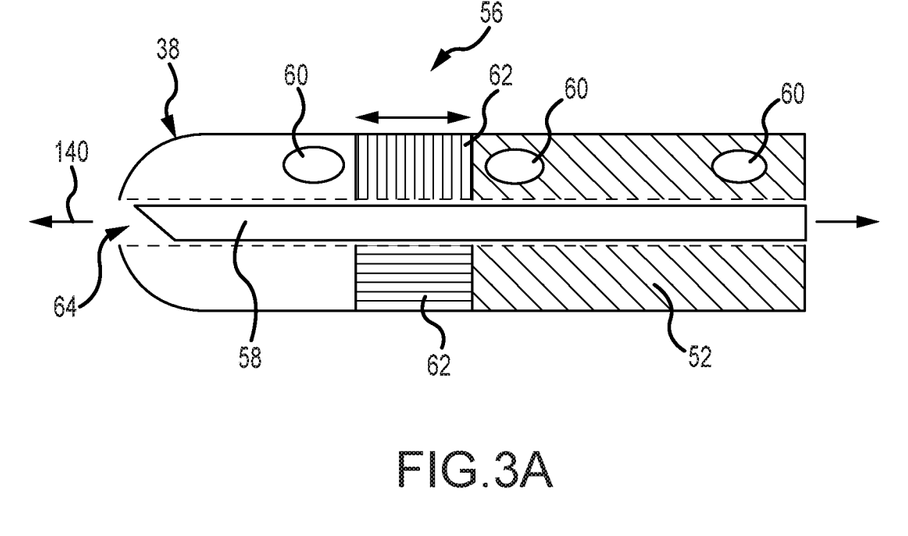
FIGS. 3A and 3B illustrates one embodiment of an injection catheter with a retracted injection needle and an extended injection needle, respectively.
Figure 3B:
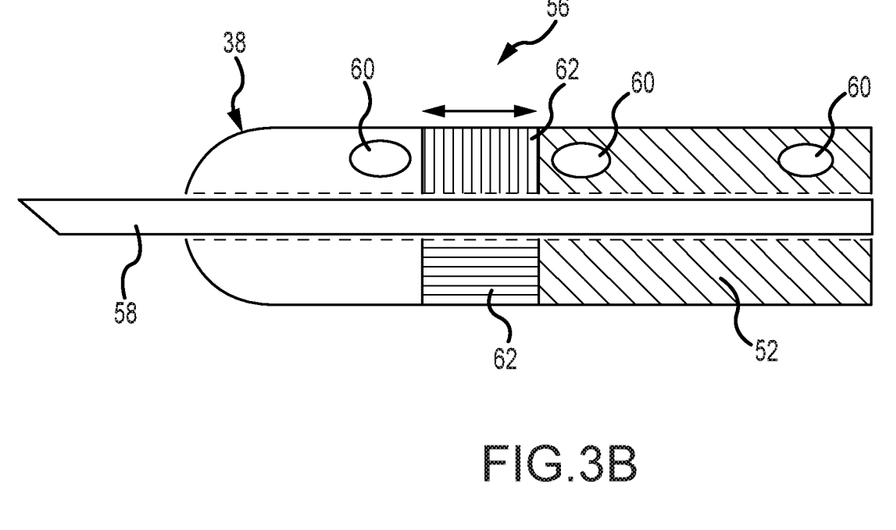

The representative therapy injection catheter 20 is provided for the injection of therapeutic substances into internal body tissues such as tissue 12 at desired locations and at desired depths. The injection catheter 20 includes an injection needle 58, which may be controllably extended and withdrawn though an internal lumen 64 of the catheter 20. See, for example, FIGS. 3A and 3B. In the illustrated embodiment, the internal lumen extends directly through the distal end of the catheter along a central axis of the catheter, though this is not a requirement. The needle is fluidly connected to a supply 44 of therapeutic solution via fluid connector attached to a rearward portion of the needle (See FIG. 1). That is, the needle may be connected to a fluid line that passes through the lumen 64 of the injection catheter 20. In such an arrangement, a short relatively rigid needle may attach to a flexible fluid lumen. In other embodiments, the therapeutic solution may be contained within an internal reservoir within the catheter. Therapeutic substances within the supply may be displaced through the needle by use of a pump device 46 (e.g., an electrically or robotically actuated pump or manual syringe barrel).

The injection catheter 20 may include a cable connector or interface 48, a handle 50, a shaft 52 having a proximal end 54 and a distal end 56 (as used herein, "proximal" refers to a direction toward the end of the catheter near the clinician, and "distal" refers to a direction away from the clinician and (generally) inside the body of a patient), the extendable needle 58, one or more position sensors 60 and one or more contact sensors 62. The catheter 20 may also include other conventional components not illustrated herein such as a temperature sensor, additional electrodes, and corresponding conductors or leads. The catheter 20 may further include signal processing circuitry and may include a memory accessible upon connection to the ECU 26 or another means for providing identifying information for catheter 20 (e.g., catheter manufacturer, model or type, potential configurations for catheter 20, etc.) to the ECU 26. The connector 48 provides mechanical, fluid and electrical connection(s) for various cables and lumens at a proximal end of catheter 20.

The handle 50 provides a location for the clinician to hold a region of interest in the body 14 catheter 20 and may further provide means for steering or guiding the shaft 52 within the body 14. For example, the handle 50 may include means to move a guidewire extending through the catheter 20 to the distal end 56 of the shaft 52 to steer the distal end 56. The handle 50 is also conventional in the art and it will be understood that the construction of the handle 50 may vary and may be absent in a fully-robotic implementation of the system.

The shaft 52 is an elongated, flexible member configured for movement within the body 14. As illustrated, the shaft 52 supports the extendable therapy needle 58, position sensors 60, contact sensors 62, associated conductors, and possibly additional electronics used for signal processing or conditioning. The shaft 52 may also permit transport, delivery, and/or removal of fluids (including irrigation fluids and bodily fluids), medicines, and/or surgical tools or instruments. The shaft 52 may be made from conventional materials such as polyurethane and typically defines one or more lumens configured to house and/or transport electrical conductors, fluids, or surgical tools. Depending on its intended use, the shaft 52 may be introduced into a blood vessel or other structure within the body 14 through a conventional introducer sheath. Once introduced, the shaft 52 may then be steered or guided through the body 14 to a desired location such as tissue 12 using guide wires or with pullwires or other means known in the art including remote catheter guidance systems (RCGS) such as a system or systems described and illustrated in U.S. Published Patent Application No. 20090247942 published Oct. 1, 2009 and titled "Robotic Catheter Manipulator Assembly"; U.S. Published Patent Application No. 20090247944 published Oct. 1, 2009 and titled "Robotic Catheter Rotatable Device Cartridge"; U.S. Published Patent Application No. 20090247993 published Oct. 1, 2009 and titled "Robotic Catheter System"; U.S. Published Patent Application No. 20090248042 published Oct. 1, 2009 and titled "Model Catheter Input Device"; International Published Patent Application No. WO 2009/120982 published Oct. 1, 2009 and titled "Robotic Catheter System With Dynamic Response"; U.S. Published Patent Application No. 20100256558 published Oct. 7, 2011 and titled "Robotic Catheter System"; and U.S. patent application Ser. No. 12/933,063 filed Sep. 16, 2010 and titled "Robotic Catheter System Input Device", the entire disclosures of which are incorporated herein by reference.

The position sensors 60 are provided to indicate the position and orientation of the catheter 20 within the coordinate system 30 defined by the medical positioning system 16. In the illustrated embodiment, the position sensors 60 comprise electrodes that are placed within the body 14 (e.g., within the heart) and within electrical fields created by exciting the patch electrodes 28. In the illustrated embodiment, the position sensors 60 are button-type electrodes. However, it will be appreciated that other electrodes type may be utilized including, without limitation, ring electrodes and/or a tip electrode (e.g., distal tip 38). The sensors 60 experience voltages that are dependent on the location between the patch electrodes 28 and the position of the sensors 60 relative to the surface of the heart. Voltage measurement comparisons made between the sensors 60 can be used to determine the position of the sensors 60 within body 14. It should also be understood that the type of position sensor used will be dependent on the type of medical positioning system used. For example, other conventional position sensing systems could be used including magnetic positioning systems such as the system available under the trademark "GMPS" or "MEDIGUIDE" from St. Jude Medical, Inc. or the system available under the trademark "CARTO" from Biosense Webster, Inc. in which the case the position sensors 60 may comprise magnetic sensors such as coils.

To better control the depth at that therapeutic substances are injected into the internal target tissue, the injection catheter 20 may further include means for sensing contact between the catheter 20 and the tissue 12. That is, the injection catheter 20 may include one or more contact sensors 62 configured to detect, for example, a force applied to, for example, a distal tip 38 of the catheter 20 resulting from contact by the distal tip with the tissue 12. Such force sensing sensors allow assessing the degree of mechanical coupling between catheter 20 and tissue 12. Along these lines, the sensors 62 may generate signals indicative of a change in resistance, voltage, capacitance, impedance or a combination thereof. In one embodiment illustrated in FIGS. 3A and 3B, sensors 62 are disposed in the distal end 56 of the catheter 20 between the distal tip 38 and the shaft 52. It should be understood, however, that the exact location of the sensors 62 may vary provided that they are located so as to sense movement of the catheter 20 in response to contact with tissue 12.

The contact sensors 62 may comprise, for example, capacitance sensors that generate a signal indicative of a change in capacitance resulting from application of a force. The force sensors 62 may also comprise piezoelectric sensors that include a piezoelectric material (in the form of a wire, film or tubes, for example) and generate a signal indicative of a change in voltage resulting from placing the piezoelectric material under stress. In another embodiment, the force sensors 62 may also comprise pressure sensitive conductive composite (PSCC) sensors (including, but not limited to, quantum tunneling conductive composite (QTC) sensors) in which the electrical resistance of the composite varies inversely in proportion to the pressure that is applied to the composite. Additional information on exemplary sensor embodiments usable with the disclosed systems, apparatuses and methods may be found in U.S. Published Patent Application No. 2011/0022045 titled "Ablation Electrodes With Capacitive Sensors for Resolving Magnitude and Direction of Forces Imparted to a Distal Portion of a Cardiac Catheter," U.S. Published Patent Application No. 2008/0161796 titled "Design of Ablation Electrode With Tactile Sensor," U.S. Published Patent Application No. 2008/0015568 titled "Dynamic Contact Assessment for Electrode Catheters," U.S. Published Patent Application No. 2007/0123764 titled "Systems and Methods for Assessing Tissue Contact," and U.S. Published Patent Application No. 2007/0100332 titled "Systems and Methods for Electrode Contact Assessment," the entire disclosures of which are incorporated herein by reference.

The catheter 20 may include one or more contact sensors 62 disposed in a plane perpendicular to a longitudinal axis 140 of the catheter 20. Where multiple sensors are used, the sensors may be disposed about the axis with regular or irregular spacing. The use of a multiple sensors 62 enables force detection in a plurality of dimensions including, for example, along the longitudinal axis 140 (stretching and compression) and laterally (bending). The sensor or sensors 62 may be mounted on a support structure within catheter 62 and may be in direct physical contact with the therapy needle or indirect contact.

In another embodiment, a pair of optically interactive elements (not shown) provides the means for sensing contact force between the catheter 20 and tissue 12. In such an embodiment, one or more optical sensors work in combination with an optically interactive surface (not shown) supported within the catheter. The optical sensor may include one or more optic fibers configured to emit and receive light energy from the electromagnetic spectrum. The optically interactive surface has a known position relative to the distal end/tip of the catheter such that a change in position, configuration and/or orientation of surface causes a change in the plane of reflection and a change in a characteristic of light (e.g., intensity, wavelength, phase, spectrum, speed, optical path, interference, transmission, absorption, reflection, refraction, diffraction, polarization and scattering) indicative of a force applied to the distal end by, for example, contact with tissue. Additional information on exemplary optical sensing assemblies usable with the present disclosure may be found in U.S. Published Patent Application No. 2008/0249522 titled "Irrigated Catheter With Improved Fluid Flow," U.S. Published Patent Application No. 2008/0275428 titled "Optic-Based Contact Sensing Assembly and System," and International (PCT) Published Patent Application No. WO 2010/078453 titled "Optic-Based Contact Sensing Assembly and System," the entire disclosures of which are incorporated herein by reference.

In any embodiment, the contact sensors 62 generate signals which may be transmitted to the ECU. For instance, such signals may be transmitted along conductors connected to the force sensors 62 and extending through shaft 52 of catheter 20. The signals may, in some embodiments, be compared to signals generated by a reference electrode coupled to the tissue 12 or electrical ground. ECU 26 may use the information generated by sensors 62 to among other things, determine the force applied to the catheter by target tissue.

The display system 24 is provided to convey information to a clinician to assist in diagnosis and/or treatment. As shown, the display system 24 may comprise one or more conventional computer monitors or other display devices. Display system 24 may provide a graphical user interface (GUI) to the clinician. The GUI may include a variety of information including, for example, an image of the geometry of a region of interest in body 14, associated electrophysiology data, therapy delivery maps and images of catheters 18, 20 and other medical devices and related information indicative of the position of catheters 18, 20 and other devices relative to the region of interest. See FIG. 2.

Examples of the type of information that may be displayed are shown in commonly assigned U.S. Pat. No. 7,263,397 titled "Method and Apparatus for Catheter Navigation and Location and Mapping in the Heart," the entire disclosure of which is incorporated herein by reference.

The ECU 26 provides a means for, at least in part, controlling the delivery of therapeutic substances from the extendable needle 58. The ECU 26 may also be a component of position and navigation system 16 and thereby provide a means for determining the geometry of a region of interest in body 14, physiologic characteristics of the region of interest and the position and orientation of catheters 18, 20 relative to the region of interest. The ECU 26 also provides a means for generating display signals used to control display system 24. ECU 26 may comprise one or more programmable microprocessors or microcontrollers or may comprise one or more ASICs. ECU 26 may include a central processing unit (CPU) and an input/output (I/O) interface through which ECU 26 may receive a plurality of input signals including signals generated by electrodes on catheters 18, 20 and feedback signals from position and navigation system 16 and generate a plurality of output signals including those used to control and/or provide data to catheters 18, 20, display system 24 and/or pump device 46. Although a single ECU 26 is shown in the illustrated embodiment for use with catheters 18, 20 and system 16, it should be understood that catheters 18, 20 and system 16 may be configured with individual ECUs.

In controlling the delivery of therapeutic substances from the extendable needle 58, the ECU 26 may further be configured to determine a degree of coupling (e.g., contact condition) and/or contact force between the distal tip 38 of the catheter and the tissue 12 and/or determine a degree of coupling/force between the needle 58 and tissue (e.g., in an embodiment where one or more force sensors are attached to the needle). Based on the degree of coupling and/or force, in conjunction with a known extension of the needle relative to the distal end of the catheter, the ECU may determine if the needle is inserted to a desired depth within the tissue. Typically, the ECU 26 may determine the degree of coupling responsive to signals indicative of contact forces between catheter 20 and tissue 12 including, for example, signals generated by the force sensors 62 described hereinabove. Additionally or alternatively, the ECU 26 may determine the degree of coupling responsive to signals indicative of impedance between a distal tip electrode 38 and tissue. As discussed in U.S. Published Patent Application No. 2010/0228247 titled "Assessment of Electrode Coupling of Tissue Ablation," U.S. Published Patent Application No. 2009/0163904 titled "System and Method for Assessing Coupling Between an Electrode and Tissue," and U.S. Published Patent Application No. 2010/0168735 titled "System and Method for Assessing Coupling Between and Electrode and Tissue," the entire disclosures of which are incorporated herein by reference, the ECU 26 may enable generation of an excitation signal from a signal source (not shown) across a path from an electrode (e.g., tip electrode 38) on the catheter 20 comprising a positive polarity connector SOURCE(+) to a return electrode located, for example, on catheter 20 or body 14 comprising a negative polarity connector SOURCE(−). This signal induces a response signal along a path from the catheter electrode which also comprises a positive polarity connector SENSE(+) to another return electrode on catheter 20 or body 14 comprising a negative polarity connector SENSE(−) that is dependent on the complex impedance at the catheter/tissue interface. Conventional circuits may be used to resolve this signal into component parts for the complex impedance at the catheter/tissue interface allowing ECU 26 to determine values for one or more components of a complex impedance between the electrode (e.g., tip electrode) and tissue 12. These components may including a resistance between the electrode and the tissue 12, a reactance there between, an impedance magnitude there between and/or an impedance phase angle there between. The ECU 26 may further compute a coupling index responsive to these components and possibly other measurements that is indicative of the degree of coupling (e.g., mechanical/force coupling), which is presented to the clinician on display system 24 or is otherwise made available for use in controlling delivery of an injectable therapeutic substance. Such impedance measurements provide measurements of contact between the electrode and tissue and may be correlated to contact forces.

Figure 4:
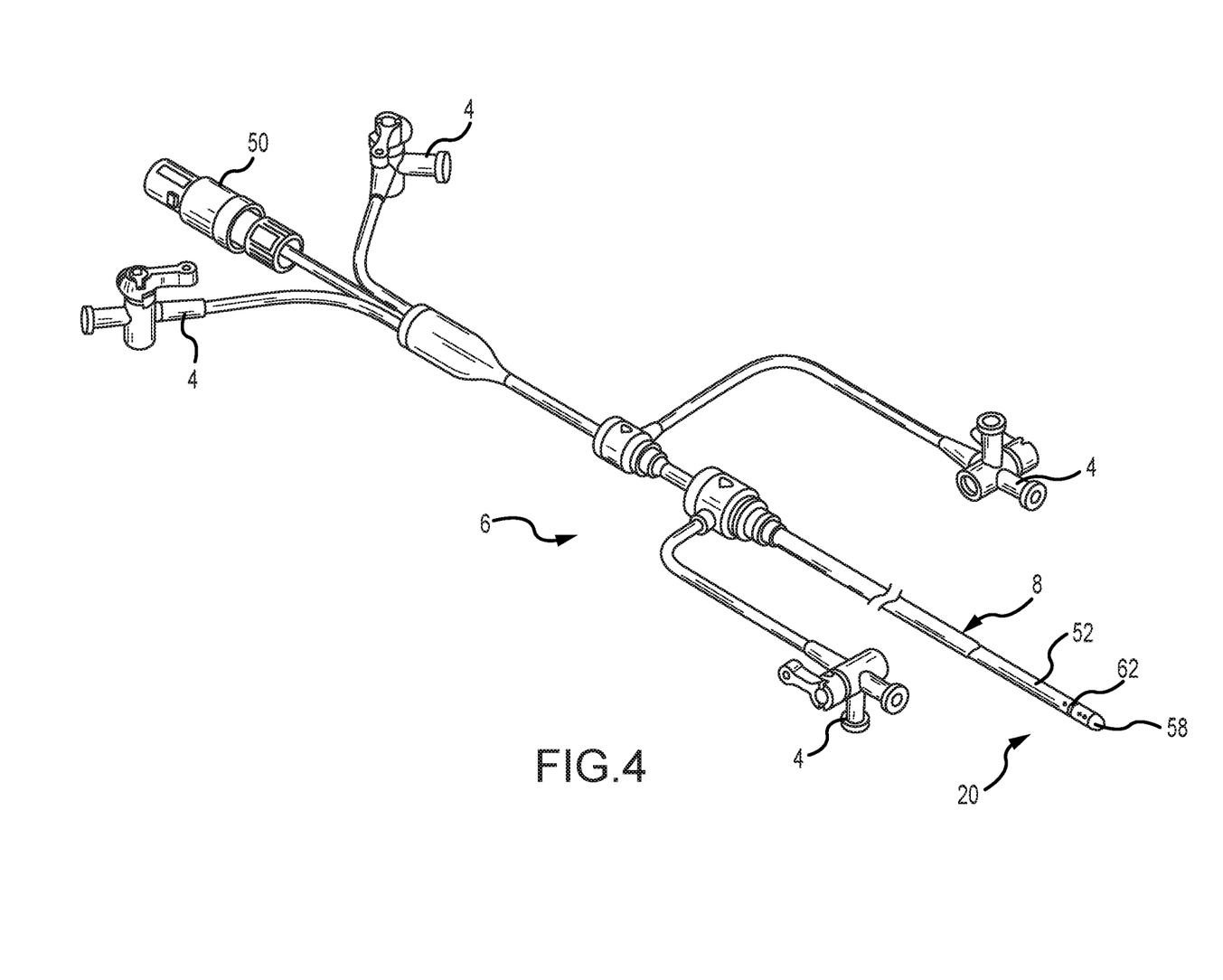
FIG. 4 illustrates an introducer sheath and catheter.

FIG. 4 illustrates the injection catheter as inserted within an introducer sheath 6. The sheath 6 is a tubular structure defining at least one lumen or longitudinal channel. The sheath 6 is used to introduce and guide the catheter 14 to a targeted internal tissue area. The catheter 14, however, may be used alone or with other guiding and introducing type devices depending on the particular procedure being performed. As shown in FIG. 4, the shaft 52 of the catheter 20 forms a tubular body extending from the proximal handle 50, through the sheath 6 and extending out of the distal end of the sheath 6. As noted the proximal handle 50 may be omitted and a proximal portion of the shaft 52 may be connected to a robotic actuator. In the particular system configuration of FIG. 4, the sheath 8 is configured to receive and guide the catheter 20 within an internal lumen to a location in the heart or other internal tissue location once the sheath 8 is pre-positioned in an appropriate location. At such time, the distal end of the catheter may extend beyond the distal end of the sheath for subsequent guidance to target locations for injection of therapeutic substances. In addition, the sheath provides a number of additional ports 4 that allow for insertion of various instruments and/or fluids into the internal lumen of the sheath and/or an internal lumen of the catheter. In one arrangement, the needle 58 may include a flexible shaft and may be inserted through a separate port. However, this is not a requirement.

Figure 2:
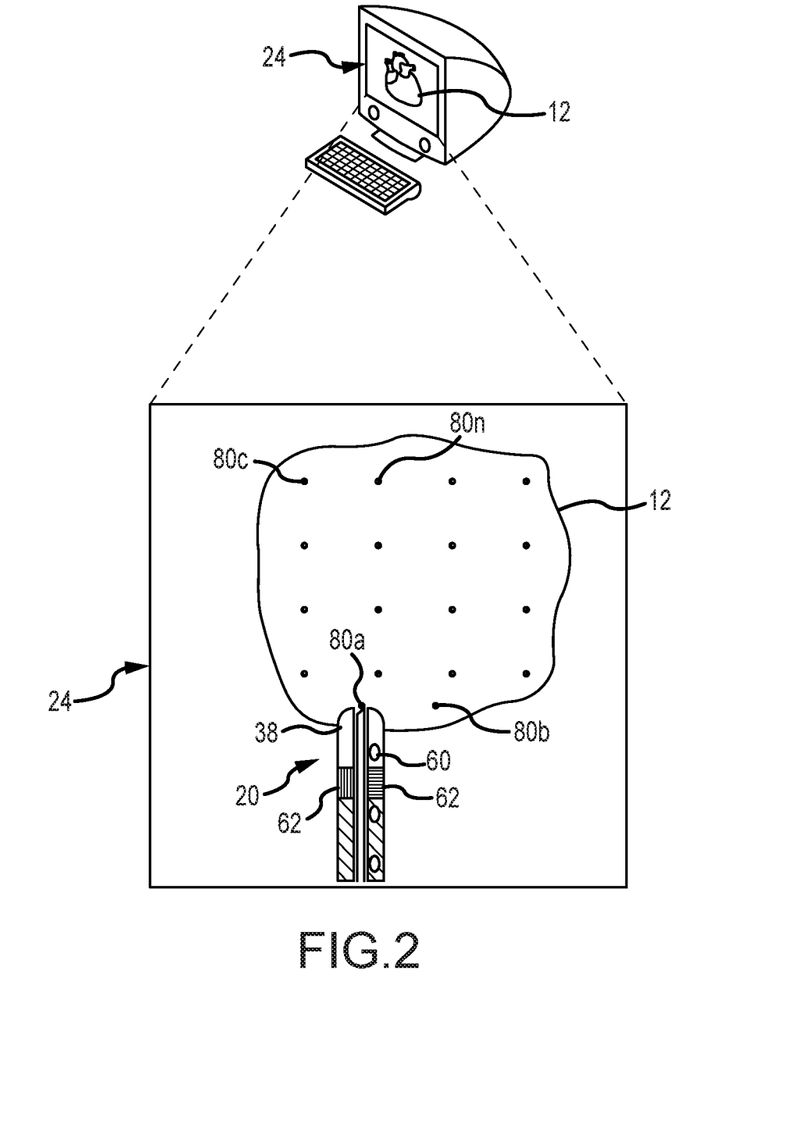
FIG. 2 illustrates a display of the exemplary catheter system.
Figure 5A:
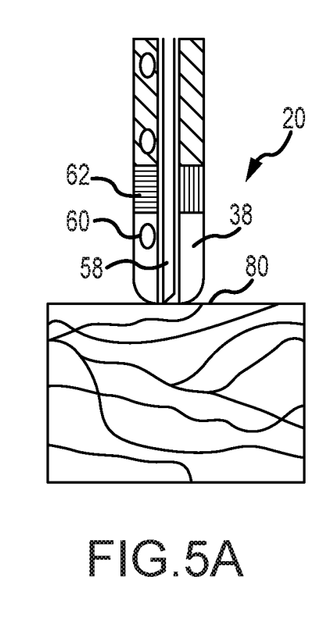
FIGS. 5A-5D illustrate insertion of a needle into tissue.
Figure 5B:
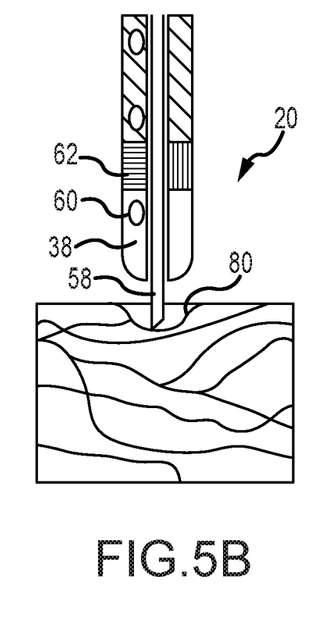

The present disclosure is based, in part, on the realization that contact between the distal end of a catheter and target tissue can adversely affect an intended insertion depth of a needle. During an internal injection procedure, the injection catheter 20 is initially guided to a target location/target tissue. This is illustrated in FIG. 2, which shows the 24 distal tip of the injection catheter 20 being positioned relative to a first internal target location 80*a*. More specifically, the ECU may generate a model of a region of interest (e.g., heart tissue 12; shown in 2D for purposes of discussion) on a display 24 along with a representation of the injection catheter 20. Based on the output of the position sensors 60, the position of the injection catheter 20 is shown relative to the region of interest. Accordingly, a clinician may guide the distal end of the catheter 20 to one or more target locations 80*a*-80*n*, which may be user selected targets or computer generated targets (e.g., grid targets). The distal end of the catheter is typically positioned such that it is brought into contact with the target location (e.g., 80*a*) prior to advancing the needle 58 to inject a therapeutic substance. This is also illustrated in FIG. 5A. However, once the catheter is disposed against the tissue surface, advancement of the injection needle 58 may result in both a deflection of the tissue surface 80 and/or displacement of the distal tip of the catheter away from the tissue surface 80. See FIG. 5B.

Figure 5C:
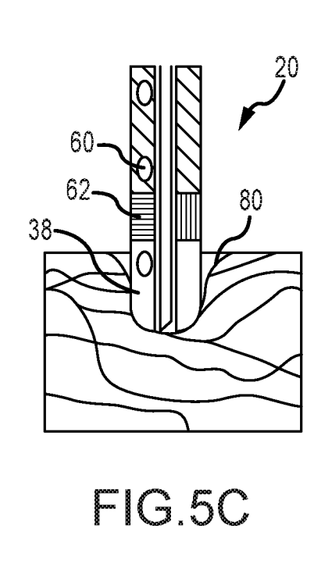

Either the displacement of the tissue or the displacement of the distal end of the catheter 20 relative to the tissue (i.e., in response to needle advancement) can result in the needle failing to insert or failing to insert to a desired depth within the tissue. As such, injection of a therapeutic substance may be too shallow. Alternatively, if the distal end of the catheter is compressed too far into the tissue, insertion of the needle may be too deep. See FIG. 5C. Accordingly, the presented systems and methods utilize contact sensing to confirm proper insertion of a needle at an internal tissue target location.

Figure 5D:
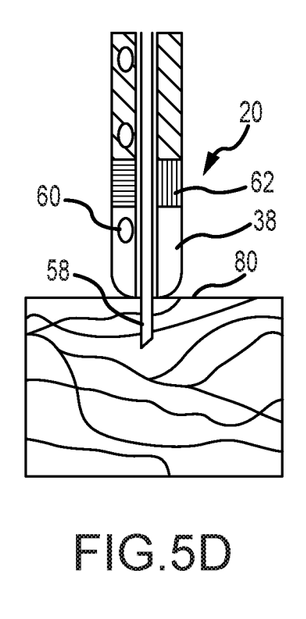
Figure 6:
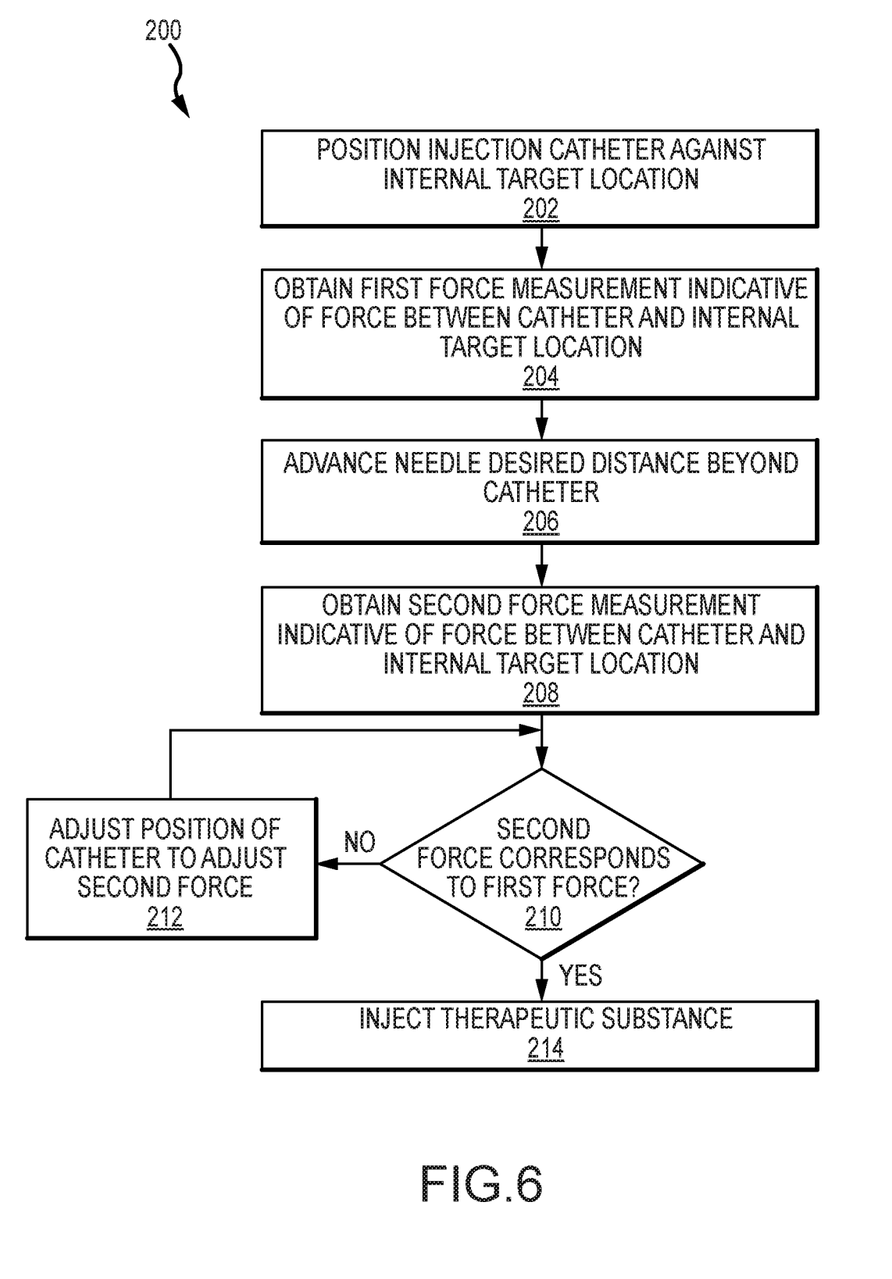
FIG. 6 illustrates one process that may be performed by the catheter system.

A first process using force sensing to confirm proper needle insertion is illustrated in FIG. 6. In this process 200, a force between the catheter and internal target location is compared (e.g., by the ECU) before and after advancement of the needle to confirm the injection catheter remains in contact with the target tissue after needle insertion. Initially, the injection catheter 20 is positioned 202 against an internal target location. Once positioned at a desired target location, a first contact measurement (e.g., force, impedance etc.) is obtained 204, which is indicative of contact between the catheter and the internal target location. See, e.g., FIG. 5A. After obtaining the first force measurement, which confirms the injection catheter 20 is in contact with the target tissue, the needle 58 is advanced 206 a desired distance beyond the injection catheter 20. After needle advancement, a second contact measurement is obtained 208, which is again indicative of the contact between the injection catheter and internal target location. The first and second contact measurements are compared 210 to determine if the second force corresponds to the first force. That is, a comparison is made to determine if the forces are equal or within a predetermined amount of one another (e.g., substantially equal). Substantially equal contact measurements confirm the injection catheter 20 remains in contact with the tissue after needle insertion and confirms insertion of the needle 58 to the desired depth within the tissue. See, e.g., FIG. 5D. At this time, the therapeutic substance may be injected 214 through the needle into the tissue. Alternatively, if the contact measurements are different (e.g., a second force is less than a first force by more than a predetermined amount) the advancement of the needle has displaced the tissue and/or displaced the injection catheter from the tissue. See, e.g., FIG. 5B. Accordingly, the position of the injection catheter may be adjusted 212 (e.g., advanced) to bring the injection catheter back into contact with the target tissue. That is, the position of the injection catheter may be adjusted until the second contact measurement corresponds to the first contact measurement. Once the second contact measurement corresponds to the first contact measurement, the injection catheter has reestablished the initial contact with the tissue and the needle is inserted to the desired depth within the tissue. Accordingly a therapeutic substance may be injected 214 through the needle.

In a variation of the process of FIG. 6, the system allows for establishing sufficient contact between the distal end of the injection catheter and the tissue to insure proper needle insertion. That is, a minimum contact may be established between the injection catheter and the target tissue location prior to needle insertion. In this regard, the contact sensors of the injection catheter provide a measurement of a magnitude of the contact between the catheter and the target tissue and the ECU determines if this contact is sufficient for subsequent needle insertion. However, it has been recognized that the sufficiency of contact between the catheter and the target tissues changes for tissues with different mechanical properties, such as tissue compliance. For example, the compliance of the relatively more compliant smooth atrial wall is different from relatively less compliant myocardial tissue. Thus, different force or contract levels may be required for different tissues.

In one embodiment, the ECU include a database or memory of contact and/or force values for use in determining sufficiency of contact between the catheter and the tissue. Such values may depend on various system parameters such as the size of the catheter, size/gauge of the needle, needle insertion depth and/or the tissue being injected. In an exemplary embodiment, contact conditions corresponding to various measurements (optical, pressure, impedance, etc.) may be predetermined, e.g., during testing for any of a wide range of tissue types for a variety of operating parameters. These predetermined force or contact measurements may be stored in memory, e.g., as tables or other suitable data structures. The processor ECU may then access the tables in memory and determine if a current contact measurement is adequate prior to needle insertion. By way of example, the ECU may receive a contact measurement and correlate that measurement based on current parameters to determine the adequacy of contact prior to needle insertion. An indication of adequate contact for needle insertion may be output to a user/clinician (e.g., at display device) upon which the needle may be advanced (e.g., manually or robotically). If the contact is inadequate, an appropriate output may be generated to allow, for example, application of additional contact force or reduction of contact force.

Figure 7A:
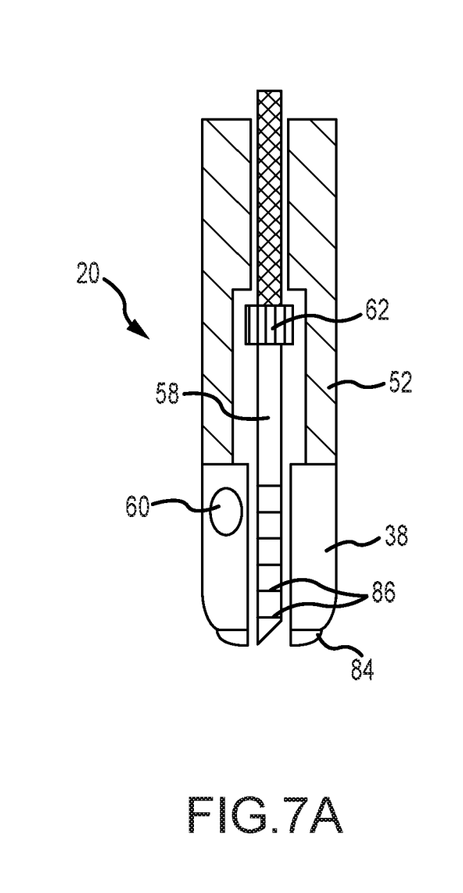
FIGS. 7A and 7B illustrates another embodiment of an injection catheter with a retracted injection needle and an extended injection needle, respectively.
Figure 7B:
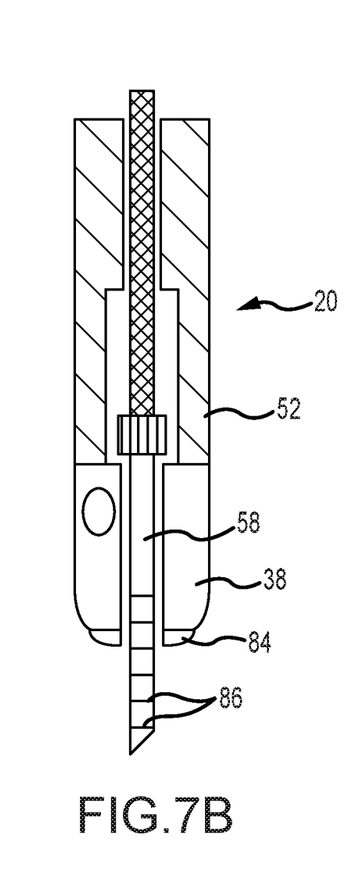

FIGS. 7A and 7B illustrate a further embodiment of an injection catheter 20. In this embodiment, the injection catheter 20 again includes an injection needle 58 and one or more position sensors 60. However, in this embodiment, a force sensor 62 is connected to the needle 58 rather than between the distal tip 38 and shaft 52 of the catheter (all electrical connections are omitted for clarity). This embodiment allows for monitoring the force applied to the needle 58 as the needle is inserted into internal tissue. Typically, the force applied to the tip of the needle will be a zero or null value when the needle is in the retracted position as shown in FIG. 7A. The force applied to the needle will increase as the needle extends into tissue. When extended to desired depth, the force on the needle returns to zero or near zero. Accordingly, such information may allow for monitoring insertion of the needle into the internal tissue. In a further embodiment, the distal tip 38 may form an impedance electrode that allows for identifying contact with the tissue. Accordingly, an output from the tip electrode 38 may be monitored in conjunction with the output of the force sensor 62 attached to the needle to monitor needle insertion. In a further embodiment, additional force sensors (not shown) may be incorporated into the shaft of the catheter and utilized in conjunction with the needle force sensor. In a further arrangement, the needle may form an impedance electrode. Accordingly, the impedance of the needle may be monitored as it is advanced. The change in the environment around the needle (e.g., insertion into tissue) will result in a change in the monitored impedance. Such a needle impedance value may, in an alternate embodiment, be utilized alone or in conjunction with additional contact measurements to confirm needle insertion.

As illustrated in FIGS. 7A and 7B, a flexible sheath 88 is disposed around the lumen extending between the needle 58 and the supply of therapeutic solution (not shown). The sheath 88 allows for applying force to the needle from a proximal location (e.g., catheter handle). Such a sheath may be incorporated into any of the catheter embodiments. The illustrated catheter also includes a needle extension sensor 84 attached to the tip of the injection catheter 20. The sensor 84 is configured to identify markings 86 disposed at known locations along the length of the needle 58. In one embodiment, the sensor 84 is a magnetic sensor and the markings 86 are magnetic bands applied about the needle 58 however, it will be appreciated that different sensors may be utilized including, for example, an impedance-based sensor. In any embodiment, the sensor 84 allows for monitoring the extension of the needle 58 relative to the catheter 20. When utilizing a catheter having the needle extension sensor 84, the ECU can generate an output that allows the clinician to monitor needle extension providing fine needle depth control. Alternatively, in a robotically controlled system, the ECU may robotically control extension of the needle to a desired extension beyond the distal end of the catheter based on the sensor output. Alternatively or in addition, markings may be provided on proximal portions of the sheath 88 and/or the needle lumen that provide an indication of the relative position of the needle to the distal end of the catheter. Such markings may allow manual or robotic needle extension. Such markings may be incorporated into any of the catheter embodiments.

Although various embodiments of the disclosed systems, apparatuses and methods have been described above with a certain degree of particularity, those skilled in the art could make numerous alterations to the disclosed embodiments without departing from the spirit or scope of this disclosure. For example, different arrangements exist for determining the position of a distal end of a catheter and for determining a force between a contact surface of a catheter and patient tissue. Further, additional arrangements exist for determining the displacement of a catheter-borne needle relative to a distal end of a catheter and/or patient tissue. Further it will be appreciated that all directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the disclosed systems, apparatuses and methods. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosed systems, apparatuses and methods as defined in the appended claims.

What is claimed is:

1. A system for internal delivery and injection of therapeutic substances into tissue within a body, comprising:
    a catheter comprising:
        a flexible elongate shaft with proximal and distal ends;
        a lumen extending through at least a portion of said shaft and having an opening exiting proximate to said distal end of said shaft;
        a first contact sensor attached to said catheter proximate to said distal end, said first contact sensor configured to generate a contact output indicative of contact between the catheter and the tissue;
        a therapy delivery needle disposed within said lumen, said therapy delivery needle fluidly connected to a supply of therapeutic solution and being selectively moveable between a retracted position disposed within said catheter and an extended position where a tip of said needle is disposed a predetermined distance beyond said opening; and
    a control unit configured to compare a first contact output
        generated when the therapy delivery needle is positioned in the retracted position with a second contact output generated when the therapy delivery needle is positioned in the extended position, to generate an output indicative of needle insertion into the tissue based on said comparison.

2. The system of claim 1, wherein, based on said comparison, said control unit is configured to generate one of:
    an output indicating said therapy delivery needle is fully inserted in the tissue when the second contact output is within a threshold amount from the first contact output; and
    an output indicating said therapy delivery needle is less than fully inserted in the tissue when the second contact output outside the threshold amount from the first contact output.

3. The system of claim 1, wherein said first contact sensor comprises an electrode, wherein the first contact output and the second contact output comprise impedance measurements indicative of physical contact between the distal end of the catheter and the tissue.

4. The system of claim 1, wherein said first contact sensor comprises a force sensor, wherein the force sensor is configured to generate the first contact output and the second contact output indicative of mechanical force between the distal end of the catheter and the tissue.

5. The system of claim 1, further comprising:
    a first position sensor attached to said catheter proximate to said distal end, said first sensor configured to generate position outputs in response to applied signals;
    a navigation system configured to receive said position outputs from said first position sensor and locate said catheter within a coordinate system including the tissue; and
    a display operatively coupled to the navigation system and configured to display a representation of said catheter relative to a model of said tissue.

6. The system of claim 5, wherein said navigation system employs electric fields to detect the position of said first position sensor within said coordinate system, wherein said first position sensor comprises an electrode.

7. The system of claim 5, wherein said navigation system employs magnetic fields to detect the position of said first position sensor within said coordinate system, wherein said first position sensor comprises a coil.

8. The system of claim 5, wherein said display is further configured to display at least one target location on or within said model of said tissue.

9. The system of claim 1, further comprising:
    a force sensor attached to said therapy delivery needle configured to generate force output indicative of forces applied to said tip of said therapy delivery needle.

10. The system of claim 1, further comprising:
    a pump to controllable displace a dosage of said therapeutic solution through said therapy delivery needle.

11. The system of claim 1, further comprising:
a sensor attached to said shaft proximate to said opening configured to sense markings on said therapy delivery needle as said therapy delivery needle moves between said retracted position and said extended position and generate an needle extension output.

* * * * *